United States Patent
Plecnik et al.

(10) Patent No.: US 11,938,044 B2
(45) Date of Patent: Mar. 26, 2024

(54) SERIES ELASTIC POWER MODULATION FOR ROBOTIC LOCOMOTION

(71) Applicant: The Regents of the University of California, Oakland, CA (US)

(72) Inventors: Mark Plecnik, Berkeley, CA (US); Ronald Fearing, Berkeley, CA (US); Duncan Haldane, Berkeley, CA (US); Justin Yim, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1134 days.

(21) Appl. No.: 16/340,051

(22) PCT Filed: Oct. 6, 2017

(86) PCT No.: PCT/US2017/055642
§ 371 (c)(1),
(2) Date: Apr. 5, 2019

(87) PCT Pub. No.: WO2018/068006
PCT Pub. Date: Apr. 12, 2018

(65) Prior Publication Data
US 2020/0046522 A1 Feb. 13, 2020

Related U.S. Application Data

(60) Provisional application No. 62/405,844, filed on Oct. 7, 2016.

(51) Int. Cl.
*B62D 57/032* (2006.01)
*A61F 2/60* (2006.01)
(Continued)

(52) U.S. Cl.
CPC .................. *A61F 2/68* (2013.01); *A61F 2/60* (2013.01); *B25J 5/00* (2013.01); *B62D 57/032* (2013.01);
(Continued)

(58) Field of Classification Search
CPC ................................. A61F 2002/708
See application file for complete search history.

(56) References Cited

U.S. PATENT DOCUMENTS

2012/0277883 A1* 11/2012 Albrecht-Laatsch ..... A61F 2/60
623/24
2014/0276262 A1* 9/2014 Kare ...................... A61H 1/024
601/34
(Continued)

FOREIGN PATENT DOCUMENTS

CN 201446986 U 5/2010

OTHER PUBLICATIONS

Haldane, D et al. "Robotic vertical jumping agility via series-elastic power modulation". Science Robotics. Dec. 6, 2016. URL: http//robotics.sciencemag.org/content/1/1/eaag2048/tab-pdf.
(Continued)

*Primary Examiner* — David H Willse
(74) *Attorney, Agent, or Firm* — Mintz Levin Cohn Ferris Glovsky and Popeo, P.C.

(57) ABSTRACT

A series elastic robotic limb may include an energy generator, an energy storage element, and a link assembly. The link assembly may include a plurality of links coupled, via one or more joints, at one or more pivot locations. The energy generator may output a first force that causes an accumulation of energy in the energy storage element while the link assembly is in a first configuration and transitions the link assembly from the first configuration to a second configuration. The energy storage element may release the energy
(Continued)

accumulated in the energy storage element when the link assembly is in the second configuration. The link assembly in the second configuration may trigger a motion of the series elastic robotic limb by at least amplifying the first force output by the energy generator and a second force associated with the energy released from the energy storage element.

18 Claims, 10 Drawing Sheets

(51) Int. Cl.
*A61F 2/68* (2006.01)
*A61F 2/70* (2006.01)
*B25J 5/00* (2006.01)
*A61F 2/76* (2006.01)
(52) U.S. Cl.
CPC .............. *A61F 2002/6827* (2013.01); *A61F 2002/6836* (2013.01); *A61F 2002/701* (2013.01); *A61F 2002/704* (2013.01); *A61F 2002/708* (2013.01); *A61F 2002/7645* (2013.01)

(56) References Cited

U.S. PATENT DOCUMENTS

2015/0321340 A1 11/2015 Smith
2016/0347387 A1* 12/2016 Hurst .................. B62D 57/032

OTHER PUBLICATIONS

Ackerman, E. "UC Berkeley's Salto Is the Most Agile Jumping Robot Ever". IEEE Spectrum. Dec. 6, 2016. URL: https//spectrum.ieee.org/automaton/robotics/robotics-hardware/uc-berkeley-salto-is-the-most-agile-jumping-robot-ever.

Galantis, A. et al., "The theoretical limits to the power output of a muscle-tendon complex with inertial and gravitational loads," Proceedings of the Royal Society B: Biological Sciences, 270(1523):1493-1498 (2003).

Haldane, D. W. et al., "A Power Modulating Leg Mechanism for Monopedal Hopping," Submitted to 2016 the IEEE/RSJ International Conference on Intelligent Robots and Systems, Daejeon, South Korea, Oct. 9-14, 2016.

Plecnik, M. et al., "Design Exploration and Kinematic Tuning of a Power Modulating Jumping Monopod," In Review for the Journal of Mechanisms and Robotics, submitted Apr. 2016.

* cited by examiner

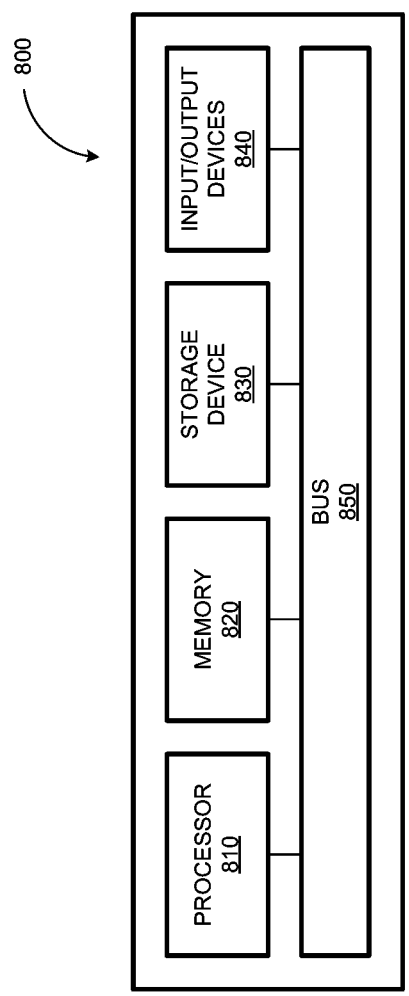

SERIES ELASTIC POWER MODULATION FOR ROBOTIC LOCOMOTION

RELATED APPLICATIONS

This application is a national phase entry of Patent Cooperation Treaty Application No. PCT/US2017/055642 filed Oct. 7, 2016, entitled "SERIES ELASTIC POWER MODULATION FOR ROBOTIC LOCOMOTION," which claims benefit of priority to U.S. Provisional Patent Application No. 62/405,844 filed on Oct. 7, 2016, entitled "SERIES ELASTIC POWER MODULATION," the disclosures of these are incorporated herein by reference in their entirety.

STATEMENT OF GOVERNMENT SPONSORED SUPPORT

This invention was made with government support under Grant Numbers 0903711 and 1549667 awarded by the National Science Foundation and Cooperative Agreement Number W911NF-08-2-0004 awarded by Army Research Laboratory. The government has certain rights in the invention.

TECHNICAL FIELD

The subject matter disclosed herein relates generally to robotics and more specifically to robotic locomotion.

BACKGROUND

Robotic locomotion may be powered by mechanical energy output by a machine such as, for example, a motor, an engine, and/or the like. For instance, a robot may include one or more motors such as, for example, electric motors, pneumatic motors, clockwork motors, and/or the like, capable of converting various types of energy (e.g., electrical energy, compressed air energy, elastic energy, and/or the like) into mechanical energy. This mechanical energy may drive mechanisms such as, for example, wheels, robotic limbs, and/or the like, that interact with the external environment to push and/or pull the mass of the robot in a desired direction.

SUMMARY

Apparatuses and methods for series elastic power modulation are provided. An apparatus for series elastic power modulation may include: an energy storage element, a link assembly, and an energy generator. The link assembly may include a plurality of links coupled, via one or more joints, at one or more pivot locations. The energy generator may be configured to output a first force. The first force may cause an accumulation of energy in the energy storage element when the link assembly is in a first configuration. The first force may further transition the link assembly from the first configuration to a second configuration. The energy storage element may be configured to release the energy accumulated in the energy storage element when the link assembly is in the second configuration. The link assembly in the second configuration may be configured to amplify the first force output by the energy generator and a second force associated with the energy released from the energy storage element. The amplified first force and second force may trigger a motion of the apparatus.

In some variations, one or more features disclosed herein including the following features can optionally be included in any feasible combination. The plurality of links may include a first link and a second link coupled via a joint. The first link and the second link may pivot about the joint in order to transition the link assembly from the first configuration to the second configuration. The first link and the second link may pivot about the joint in response to the first force output by the energy generator.

In some variations, the transition to the second configuration may maximize a mechanical advantage associated with the link assembly. The amplification of the first force and the second force may be at a maximum when the mechanical advantage associated with the link assembly is maximized. A quantity of the plurality of links, a respective length of each of the plurality of links, a respective mass of each of the plurality of links, and/or the one or more pivot locations may be configured such that the mechanical advantage associated with the link assembly increases as the link assembly transitions from the first configuration to the second configuration.

In some variations, the first configuration may be a crouched configuration and the second configuration may be an extended configuration. The apparatus may further include a foot. The amplified first force and second force may act on the foot to trigger the motion of the apparatus. The action of the amplified first force and second force on the foot may trigger a ground reaction force when the foot makes contact with a surface. The ground reaction force may cause the motion of the apparatus. The transition of the link assembly may cause the foot to move in a straight path with respect to a body of the apparatus such that the ground reaction force traverses a center of mass of the apparatus and lacks rotational moments that cause a spinning motion of the apparatus.

In some variations, the motion may be a jumping motion.

A method for series elastic power modulation may include: outputting, by an energy generator comprising an apparatus, a first force, the apparatus further comprising an energy storage element and a link assembly that includes a plurality of links coupled, via one or more joints, at a one or more pivot locations, the first force causing an accumulation of energy in the energy storage element when the link assembly is in a first configuration, and the first force further transitioning the link assembly from the first configuration to a second configuration; in response to the link assembly being transitioned to the second configuration, releasing, by the energy storage element, the energy accumulated in the energy storage element; and amplifying, by the link assembly in the second configuration, the first force output by the energy generator and a second force associated with the energy released from the energy storage element, the amplified first force and second force triggering a motion of the apparatus.

In some variations, the plurality of links may include a first link and a second link coupled via a joint. The first force may transition the link assembly from the first configuration to the second configuration by at least causing the first link and the second link to pivot about the joint. The transition to the second configuration may maximize a mechanical advantage associated with the link assembly. The amplification of the first force and the second force may be at a maximum when the mechanical advantage associated with the link assembly is maximized.

In some variations, a quantity of the plurality of links, a respective length of each of the plurality of links, a respective mass of each of the plurality of links, and/or the one or more pivot locations may be configured such that the mechanical advantage associated with the link assembly increases as the link assembly transitions from the first configuration to the second configuration. The first configuration may be a crouched configuration and the second configuration may be an extended configuration. The amplified first force and second force may be delivered to a foot of the apparatus. The amplified first force and second force may act on the foot to trigger the motion of the apparatus. The action of the amplified first force and second force on the foot may trigger a ground reaction force, in response to the foot making contact with a surface. The ground reaction force may cause the motion of the apparatus. The transition of the link assembly may cause the foot to move in a straight path with respect to a body of the apparatus such that the ground reaction force traverses a center of mass of the apparatus and lacks rotational moments that cause a spinning motion of the apparatus.

In some variations, the motion may be a jumping motion.

An apparatus for series elastic power modulation may include: means for storing energy; means for providing mechanical advantage; and means for generating energy. The means for generating energy may output a first force. The first force may cause an accumulation of energy in the means for storing energy when the means for providing mechanical advantage is in a first configuration. The first force may further transition the means for providing mechanical advantage from the first configuration to a second configuration. The means for storing energy may release the energy accumulated in the means for storing energy when the means for providing mechanical advantage is in the second configuration. The means for providing mechanical advantage in the second configuration may amplify the first force output by the means for generating energy and a second force associated with the energy released from the means for storing energy. The amplified first force and second force may trigger a motion of the apparatus The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a leg assembly of a jumping robot, it should be readily understood that such features are not intended to be limiting and that the features and elements described herein can be applied to other robotic systems. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 8 depicts a block diagram illustrating a computing system, in accordance with some example embodiments.

When practical, similar reference numbers denote similar structures, features, or elements.

DETAILED DESCRIPTION

The power output by a robotic limb may be limited by the power output of the motor driving the robotic limb. To increase the power output of the robotic limb beyond the power output of the motor, the robotic limb may be coupled with an energy storage element such as, for example, an elastic, a spring, and/or the like. For example, while the spring is held static by a latch, energy may accumulate in the spring as the motor exerts a force (e.g., torque) against the spring that deforms (e.g., compresses, twists, winds, and/or the like) the spring. Opening the latch may release the energy stored in the deformed spring. The resulting force may act on the robotic limb to cause a motion such as, for example, a jump. However, this release of energy may be difficult to control and may cause the robotic limb to move in an erratic manner. Moreover, repeating the same motion may require closing the latch beforehand, thereby imposing a significant time delay that prevents the motion from being repeated at a high frequency.

In some example embodiments, a series elastic robotic limb may be configured to store energy to and/or release energy from an energy storage element (e.g., a spring and/or the like) without any latches. Instead, energy may be stored to and/or released from the energy storage element as the robotic limb transitions from one configuration to another configuration. For example, the robotic limb may be coupled with a motor. While the robotic limb is in a crouched configuration, force (e.g., torque) output by the motor may be transferred to the energy storage element and cause an accumulation of energy in the energy storage element. The force output by the motor may further transition the robotic limb from the crouched configuration to the extended configuration. When the robotic limb reaches the extended configuration, the force output by the motor and the force from the energy released from the energy storage element may both act on the robotic limb to cause a motion, such as, for example, a jump.

In some example embodiments, transitioning the robotic limb from one configuration to another configuration may increase the mechanical advantage associated with the robotic limb. For instance, the robotic limb may be configured to exhibit a minimum mechanical advantage in the crouched configuration and a maximum mechanical advantage in the extended configuration. As used herein, mechanical advantage may refer to the force amplification achieved by the robotic limb. Accordingly, when the robotic limb is in the crouched configuration, force output by the motor may cause an accumulation of energy in the energy storage element but is not amplified by the robotic limb. By contrast, when the robotic limb is in the extended configuration, the robotic limb may amplify both the force output by the motor and the force output by the energy storage element, thereby maximizing the power of the resulting motion (e.g., jump and/or the like).

Figure 1B:
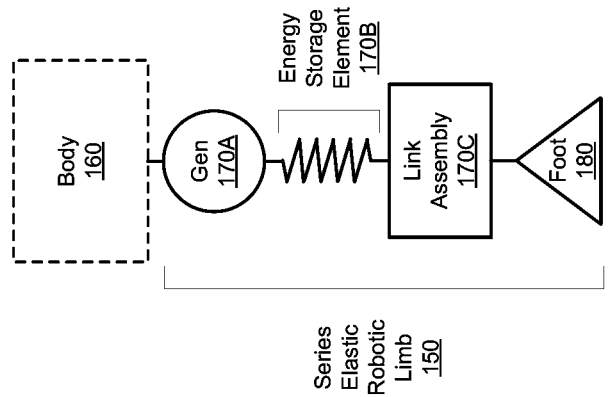
FIG. 1B depicts a block diagram illustrating a series elastic robotic limb, in accordance with some example embodiments.
Figure 1A:
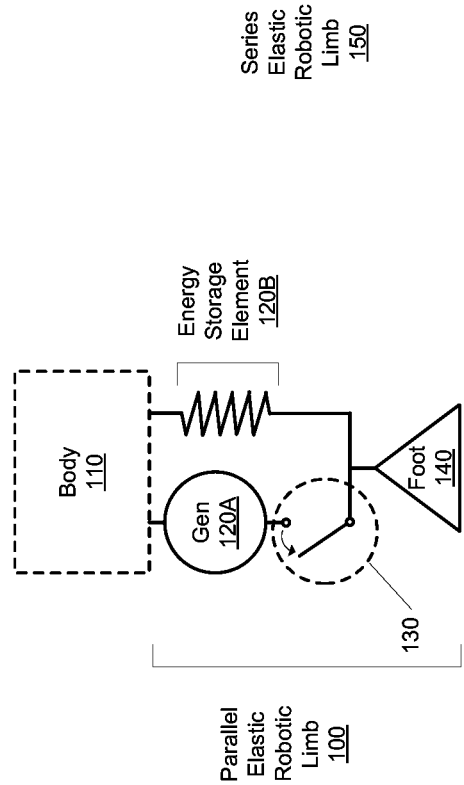
FIG. 1A depicts a block diagram illustrating a parallel elastic robotic limb, in accordance with some example embodiments.

FIG. 1A depicts a block diagram illustrating a parallel elastic robotic limb 100, in accordance with some example embodiments. Referring to FIG. 1A, the parallel elastic robotic limb 100 may be coupled to a body 110 of, for example, a robot. Furthermore, the parallel elastic robotic limb 100 may include an energy generator 120A, an energy storage element 120B, a latch 130, and a foot 140. As shown in FIG. 1A, the energy storage element 120B may be a spring, which may be held static by the latch 130. Here, the energy storage element 120B may be disposed in a parallel configuration relative to the energy generator 120A. Meanwhile, the energy generator 120A may be any machine capable of outputting mechanical energy including, for example, an engine, a motor, and/or the like.

To increase the power output of the parallel elastic robotic limb 100 to beyond the power output of the energy generator 120A, the energy generator 120A may exert a force (e.g., torque) against the energy storage element 120B while the energy storage element 120B is held static by the latch 130. Opening the latch 130 may release the energy that accumulated in the energy storage element 120B. This energy may be delivered to the foot 140 and cause the parallel elastic robotic limb 100 to perform a motion such as, for example, a jump. The motion of the parallel elastic robotic limb 100 may move the body 110, for example, by propelling the body 110. However, as noted, the energy that is released by opening the latch 130 may be difficult to control and may cause the parallel elastic robotic limb 100 to move in an erratic manner. Furthermore, operating the latch 130 may impose significant time delay that prevents the parallel elastic robotic limb 100 from executing high frequency motions. As such, the parallel elastic robotic limb 100 may be unsuitable for various applications.

FIG. 1B depicts a block diagram illustrating a series elastic robotic limb 150, in accordance with some example embodiments. Referring to FIGS. 1A-B, the series elastic robotic limb 150 may include an energy generator 170A, an energy storage element 170B, a link assembly 170C, and a foot 180. The series elastic robotic limb 150 may be coupled with a body 160 of, for example, a robot. In some example embodiments, the series elastic robotic limb 150 may be latch free. To increase power output, the series elastic robotic limb 150 may vary its mechanical advantage as the series elastic robotic limb 150 transitions from one configuration to another configuration. For example, the mechanical advantage of the link assembly 170C may vary as the link assembly 170C transitions from a crouched configuration to an extended configuration. The mechanical advantage associated with the link assembly 170C may increase the power delivered by the energy generator 170A and the energy storage element 170B. Thus, transitioning the link assembly 170C from one configuration to another configuration may increase the power output of the series elastic robotic limb 150 beyond the power output of the energy generator 170A. It should be appreciated that increasing the power output of the series elastic robotic limb 150 may increase the range of the motion performed by the series elastic robotic limb 150. For instance, increasing the power output of the series elastic robotic limb 150 may increase the height of the jumping motion performed by the series elastic robotic limb 150. Furthermore, the series elastic robotic limb 150 may increase power output without any latches, thereby removing the time delays associated with operating a latch as in the parallel elastic robotic limb 100.

Figure 2A:
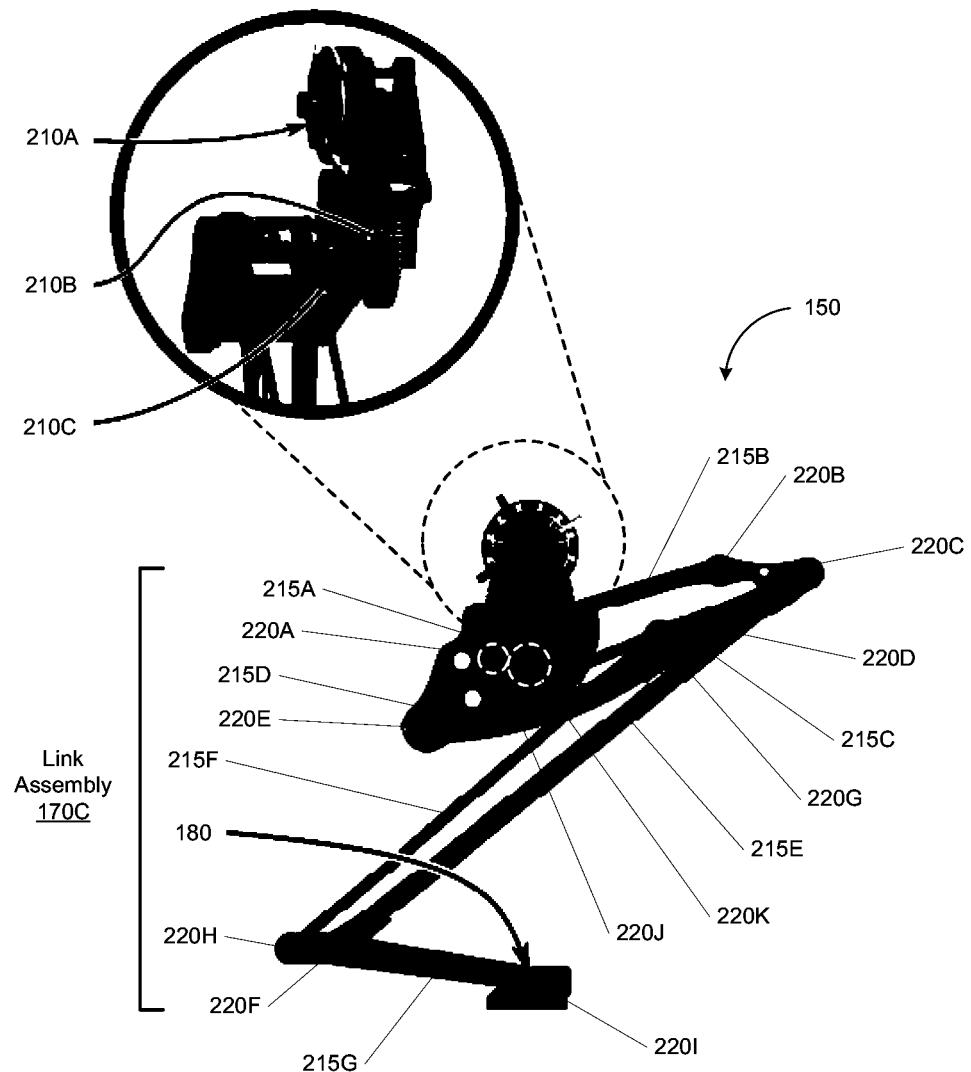
FIG. 2A depicts a series elastic robotic limb, in accordance with some example embodiments.
Figure 2B:
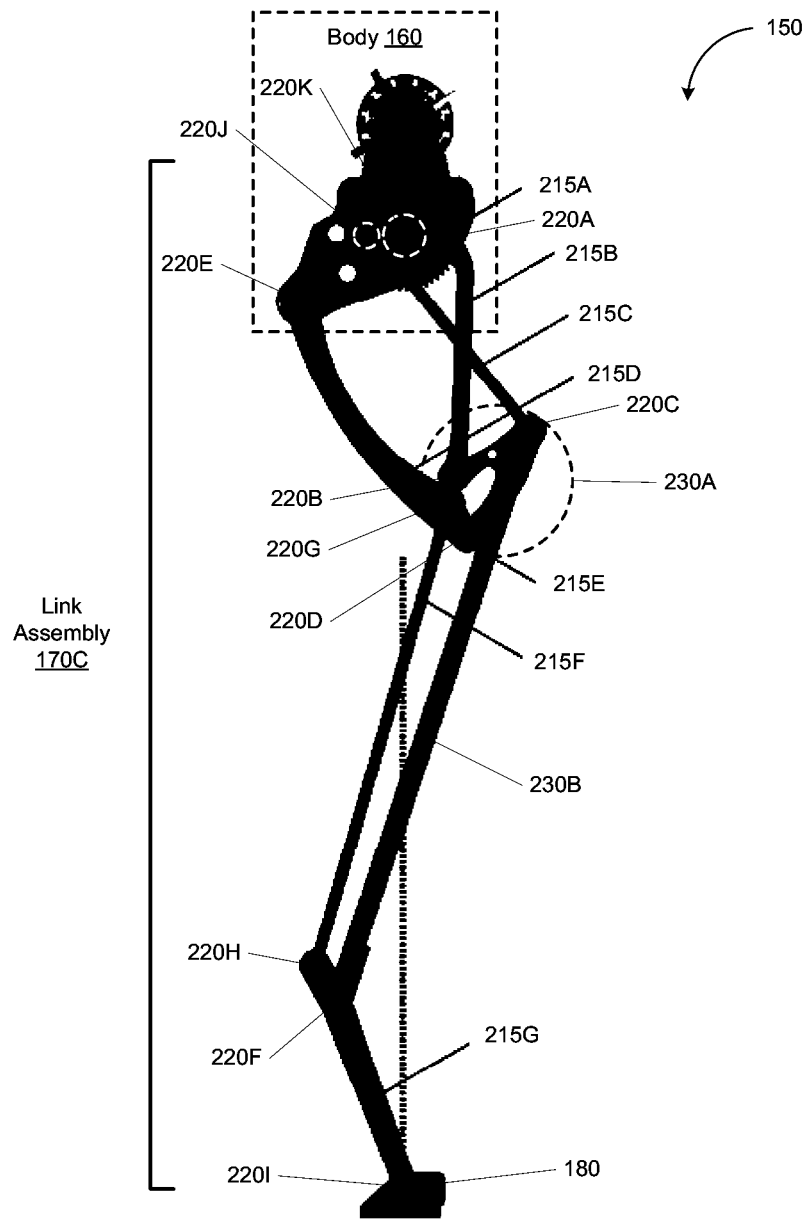
FIG. 2B depicts a series elastic robotic limb, in accordance with some example embodiments.
Figure 2C:
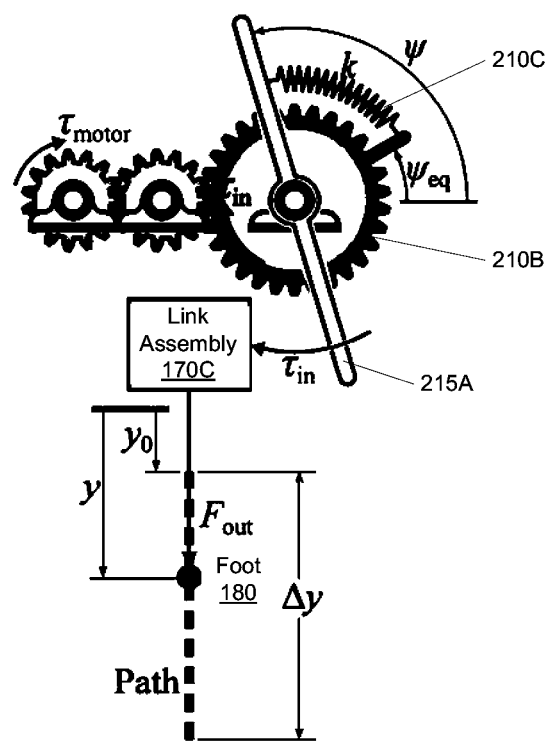
FIG. 2C depicts a series elastic robotic limb, in accordance with some example embodiments.

To further illustrate, FIGS. 2A-C depicts the series elastic robotic limb 150, in accordance with some example embodiments. FIG. 2A depicts the series elastic robotic limb 150 when the link assembly 170C is in a crouched configuration while FIG. 2B depicts the series elastic robotic limb 150 when the link assembly 170C is in an extended configuration.

Referring to FIGS. 2A-B, the link assembly 170C of the series elastic robotic limb 150 may include a plurality of moving links including, for example, a first link 215A, a second link 215B, a third link 215C, a fourth link 215D, a fifth link 215E, a sixth link 215F, and a seventh link 215G. As shown in FIG. 2A-B, the fifth link 215E may include a wishbone joint 230A that is rigidly affixed to a first end of a straight link 230B. The first link 215A, the second link 215B, the third link 215C, the fourth link 215D, the fifth link 215E, the sixth link 116F, and the seventh link 215G may be connected at one or more pivot locations. For example, two or more links may be coupled via one or more joints. These joints may be any type of joint including, for example, revolute joints, geared revolute joints, ball and socket joints, prismatic joints, and/or the like, that enables the two or more coupled links to pivot, articulate, and/or rotate along one or more axes.

As shown in FIGS. 2A-B, the first link 215A may be coupled with the body 160 of the robot via an eleventh joint 220K. The first link 215A may further be coupled with the second link 215B and the third link 215C. For instance, in some example embodiments, a first end of the first link 215A may be coupled with a first end of the second link 215B via a first joint 220A while a second end of the first link 215B may be coupled with a first end of the third link 215C via a tenth joint 215J. Meanwhile, the second link 215B, the third link 215C, and the fourth link 215D may be coupled with the fifth link 215E. For example, a second end of the second link 215B, a second end of the third link 215C, and a first end of the fourth link 215D may be coupled with a first end of the fifth link 215E, for example, at the wishbone joint 230A. For instance, the second end of the second link 215B may be coupled with the wishbone joint 230A via a second joint 220B while the second end of the third link 215C may be coupled with the wishbone joint 230A via a third joint 220C. Meanwhile, the first end of the fourth link 215D may be coupled with the wishbone joint 230A via a fourth joint 220D while a second end of the fourth link 215D may be coupled, via a fifth joint 220E, with the body 160 of the robot.

In some example embodiments, the first end of the fourth link 215D may be further coupled with a first end of the sixth link 215F via a seventh joint 220G. The second end of the sixth link 215F may be coupled with a first end of the seventh link 215G via an eighth joint 220H. Meanwhile, a second end of the fifth link 215E (e.g., a second end of the straight link 230B) may be coupled with the seventh link 215G via a sixth joint 220F. Alternatively and/or additionally, a second end of the seventh link 215G may be coupled with the foot 180 via a ninth joint 220I. It should be appreciated that this ninth joint 220I may be optional. As such, the link assembly 170C may or may not pivot with respect to the foot 180.

Although the link assembly 170C of the series robotic limb 150 is shown to include eight links, it should be appreciated that the link assembly 170C may include a different quantity of links than shown in FIGS. 2A-C. The links included in the link assembly 170C may also have different masses, lengths, and/or pivot locations than shown. In some example embodiments, the quantity of links included in the link assembly 170C, the respective lengths of the links, the respective masses of the links, and/or the pivot locations may be configured to achieve a variable mechanical advantage profile. For instance, the quantity of links, the respective lengths of the links, the respective masses of the links, and/or the pivot locations may be configured such that the mechanical advantage associated with link assembly 170C varies depending on the configuration of the link assembly 170C. According to some example embodiments, the quantity of links, the respective lengths of the links, the respective masses of the links, and/or the pivot locations may be configured such that the mechanical advantage of the link assembly 170 increases when the link assembly 170C transitions from a crouched configuration to an extended configuration.

Referring again to FIG. 2A, the energy generator 170A of the series elastic robotic limb 150 may be a motor 210A coupled with one or more gears 210B. Meanwhile, the energy storage element 170B may be a spring 210C. Force (e.g., torque) output by the motor 210A may deform the spring 210C and cause an accumulation of energy in the spring 210C. The force output by the motor 210A may further transition the link assembly 170C from one configuration to another configuration, for example, from the crouched configuration shown in FIG. 2A to the extended configuration shown in FIG. 2B. As shown in FIG. 2C, the force output by the motor 210A may act the gears 210B, which may be coupled with the first link 215A of the link assembly 170C (or another link). Here, the first link 215A may serve as an input link that transfers the force output by the motor 210A to the rest of the link assembly 170C. In doing so, the force output by the motor 210A may act on the link assembly 170C to transition the link assembly 170C from one configuration (e.g., a crouched configuration) to another configuration (e.g., an extended configuration).

To transition from the crouched configuration shown in FIG. 2A to the extended configuration shown in FIG. 2B, one or more of the links forming the link assembly 170C may pivot, articulate, and/or rotate about the first joint 220A, the second joint 220B, the third joint 220C, the fourth joint 220D, the fifth joint 220E, the sixth joint 220F, the seventh joint 220G, the eighth joint 220H, the ninth joint 220I, the tenth joint 220J, and/or the eleventh joint 220K. For instance, as the link assembly 170C transitions from the crouched configuration to the extended configuration, the third link 215C and the fifth link 215E pivot at the third joint 220C, the fifth link 215E and the seventh link 215G may pivot at the sixth joint 220F, and/or the sixth link 215F and the seventh link 215G may pivot at the eighth joint 220H.

According to some example embodiments, the energy accumulated in the spring 210C may be released once the link assembly 170C reaches the extended configuration shown in FIG. 2B. When the link assembly 170C is in the extended configuration, the force (e.g., torque) output by the motor 210A and the force (e.g., torque) of the energized spring 210C may both act on the series elastic robotic limb 150 to cause a motion. For instance, the forces (e.g., torques) from the motor 210A and the spring 210C may be delivered to the foot 180 of the series elastic robotic limb 150, thereby causing the series elastic robotic limb 150 to execute a jumping motion.

In some example embodiments, the link assembly 170C may be configured to exhibit a variable mechanical advantage profile. For example, the link assembly 170C may provide increasing mechanical advantage as the link assembly 170C transitions from one configuration to another configuration. The variable mechanical advantage profile of the link assembly 170C may enable the series elastic robotic limb 150 to store energy and/or release energy without any latches.

To further illustrate, the link assembly 170C may exhibit low mechanical advantage when the link assembly 170C is in a certain configuration such as, for example, the crouched configuration shown in FIG. 2A. When the mechanical advantage of the link assembly 170C is low, the force (e.g., torque) output by the motor 210A may energize the spring 210C. However, this force may not be amplified by the link assembly 170C. As such, a minimal quantity of force is delivered to the foot 180. By contrast, the mechanical advantage of the link assembly 170C may increase as the link assembly 170C is transitioned, by the force output by the motor 210A, to a different configuration such as, for example, the extended configuration shown in FIG. 2B. According to some example embodiments, the mechanical advantage of the link assembly 170C may be at a maximum when the link assembly 170C is in the extended configuration. As such, the link assembly 170C in the extended configuration may amplify both the force output by the motor 210A and the force from the energized spring 210C. This results in the delivery of a large quantity of force to the foot 180. It should be appreciated that the quantity of this force may exceed the power output of the motor 210A. This force may cause the series elastic robotic limb 150 to perform a motion such as, for example, a jump and/or the like.

In some example embodiments, transitioning the link assembly 170C from one configuration (e.g., a crouched configuration) to another configuration (e.g., an extended configuration) may increase the mechanical advantage associated with the link assembly 170C. As noted, mechanical advantage may refer to the force amplification achieved by the series elastic robotic limb 150. For instance, the mechanical advantage MA of the series elastic robotic limb 150 may be determined based on Equation (1) below.

$$MA = \frac{F_{ext}}{F_A} \qquad (1)$$

wherein $F_{ext}$ may be the force delivered to the foot 180 of the series elastic robotic limb 150 and $F_A$ may be the forces output by the motor 210A and/or the spring 210C.

According to some example embodiments, the mechanical advantage of the link assembly 170C may be at a minimum when the link assembly 170C is in one configuration such as, for example, the crouched configuration shown in FIG. 2A. Alternatively and/or additionally, the mechanical advantage of the link assembly 170C may be at a maximum when the link assembly 170C is in a different configuration such as, for example, the extended configuration shown in FIG. 2B.

Figure 3:
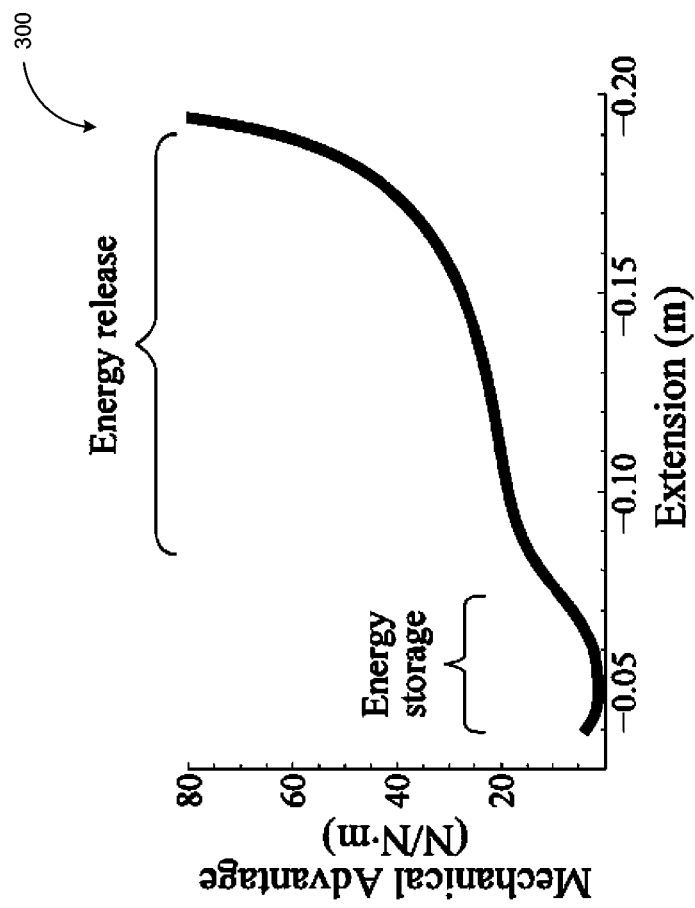
FIG. 3 depicts a graph illustrating the mechanical advantage profile of a series elastic robotic limb, in accordance with some example embodiments.

To further illustrate, FIG. 3 depicts a graph 300 illustrating the mechanical advantage profile of the link assembly 170, in accordance with some example embodiments. Referring to FIG. 3, the graph 300 depicts the relationship between the mechanical advantage of the link assembly 170C and the configuration of the link assembly 170C. For instance, as shown in FIG. 3, the mechanical advantage of the link assembly 170C may be low when the link assembly 170 is in the crouched configuration. Here, the force (e.g., torque) output by the motor 210A may cause an accumulation of energy in the spring 210C but is only subject to minimal amplification by the series elastic robotic limb 150. This initial accumulation of energy is shown as an energy storage phase in the graph 300. Due to a lack of mechanical advantage during the energy storage phase, a minimal quantity of force may be delivered to the foot 180.

By contrast, the mechanical advantage of the link assembly 170C may increase as the link assembly 170C begins to transition into the extended configuration. As shown in FIG. 3, the series elastic robotic limb 150 may enter an energy release phase as the link assembly 170C transitions from the crouched configuration to the extended configuration. During the energy release phase, the force output by the motor 210A and the force of the energy released from the spring 210C may be delivered to the foot 180 to cause a motion such as, for example, a jump. Furthermore, the mechanical advantage of the link assembly 170C, which may be maximized when the link assembly 170C is fully extended, may further amplify these forces to maximize the power of the motion. It should be appreciated that amplifying the forces delivered to the foot 180 may increase the range of the resulting motion such as, for example, the height of the jumping motion performed by the series elastic robotic limb 150.

In some example embodiments, the transition of the link assembly 170C from the crouched configuration to the extended configuration may occur at a high speed (e.g., less than 200 milliseconds). This transition may be repeated at a high frequency, thereby allowing the series elastic robotic limb 150 may repeat the same motion at a high frequency. Moreover, as shown in FIGS. 2A-B, the link assembly 170C may be configured to control the directionality of the force delivered to the foot 180, thereby controlling the directionality of the resulting motion. For example, as the link assembly 170C transitions from the crouched configuration to the extended configuration, the link assembly 170 may move the foot 180 in a straight line with minimal horizontal displacement until the foot 180 makes contact with the external environment (e.g., a surface). By keeping the path of the foot 180 as a straight line with respect to the body 160, the foot 180 may trigger a ground reaction force that traverses through the center of mass of the body 160 of the robot. This ground reaction force may lack rotational moments and may thus cause a rotation free jump in which the body 160 is propelled straight upward without any spinning motion.

Figure 4:
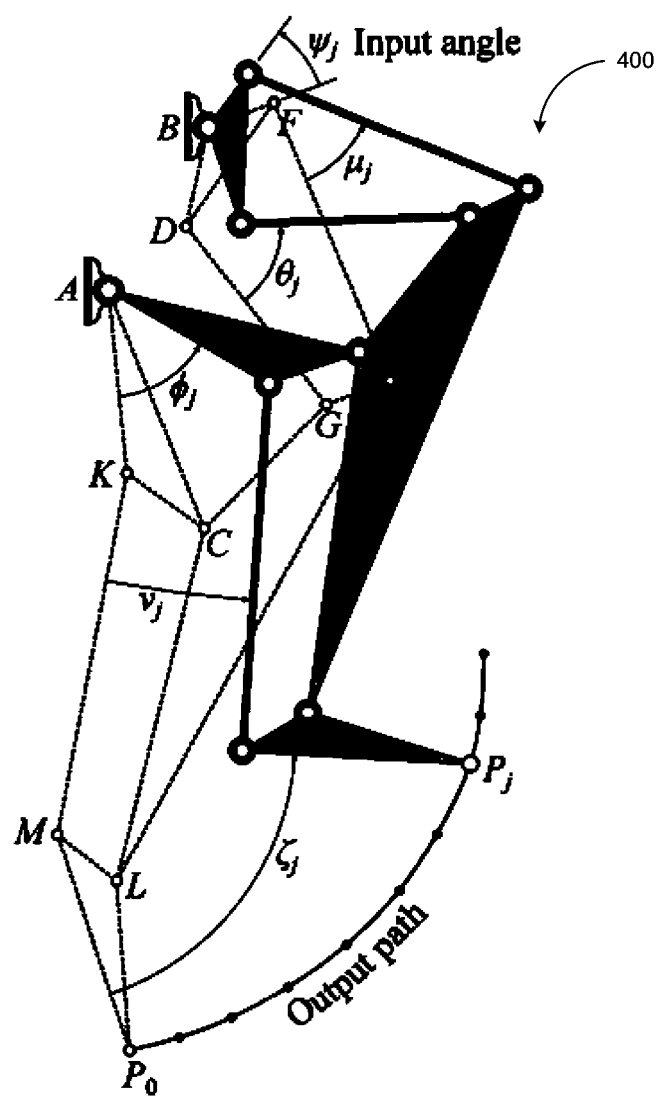
FIG. 4 depicts a link assembly, in accordance with some example embodiments.

FIG. 4 depicts a link assembly 400, in accordance with some example embodiments. In some example embodiments, the link assembly 400 may implement the link assembly 170C described with respect to FIGS. 1B and 2A-C.

Referring to FIG. 4, the link assembly 400 may include eight bars that form seven links ACK, CGHL, BDF, DG, FH, KM, and LMP that move with respect to the body of a robot. Transitioning the link assembly 400 to a j-th configuration may displace the links ACK, CGHL, BDF, DG, FH, KM, and LMP. The displacement of the links ACK, CGHL, BDF, DG, FH, KM, and LMP may be quantified by the respective angular displacement $\phi_j$, $\rho_j$, $\psi_j$, $\theta_j$, $\mu_j$, $\nu_j$, and $\zeta_j$. Furthermore, the rotation of the links may be determined based on Equation (2) below:

$$Q_j = e^{i\phi_j}, R_j = e^{i\rho_j}, S_j = e^{i\psi_j}, T_j = e^{i\theta_j}, U_j = e^{i\mu_j}, Z_j = e^{i\zeta_j} \quad (2)$$

Equations (3)-(6) below may express the geometry of the ACK, CGHL, BDF, DG, FH, KM, and LMP.

$$A + Q_j(C-A) + R_j(G-C) = B + S_j(D-B) + T_j(G-D) \quad (3)$$

$$A + Q_j(C-A) + R_j(H-C) = B + S_j(F-B) + U_j(H-F) \quad (4)$$

$$A + Q_j(C-A) + R_j(L-C) + Z_j(P_0-L) = P_j \quad (5)$$

$$A + Q_j(K-A) + V_j(M-K) + Z_j(P_0-M) = P_j \quad (6)$$

Equations (7) and (8) below may define intermediate variables $d_j$ and $f_j$.

$$d_j = A - P_j + Q_j(C-A) + Z_j(P_0-L) \quad (7)$$

$$f_j = A - P_j + Q_j(K-A) + Z_j(P_0-M) \quad (8)$$

Based on the intermediate variables $d_j$ and $f_j$, Equations (3)-(6) may be simplified into Equations (9)-(12) below. Equations (9)-(12) may express the geometric constraints of the links ACK, CGHL, BDF, DG, FH, KM, and LMP. It should be appreciated that the overbars may denote conjugates.

$$d_j \overline{d_j} = (L-C)(\overline{L}-\overline{C}) \quad (9)$$

$$f_j \overline{f_j} = (M-K)(\overline{M}-\overline{K}) \quad (10)$$

$$((a_j-b_j)(L-C)-d_j(G-C))((\overline{a}_j-\overline{b}_j)(\overline{L}-\overline{C})-\overline{d}_j(\overline{G}-\overline{C})) = (G-D)(\overline{G}-\overline{D})(L-C)(\overline{L}-\overline{C}) \quad (11)$$

$$((a_j-c_j)(\overline{L}-\overline{C})-d_j(H-C))((\overline{a}_j-\overline{c}_j)(\overline{L}-\overline{C})-\overline{d}_j(\overline{G}-\overline{C})) = (H-F)(\overline{H}-\overline{F})(L-C)(\overline{L}-\overline{C}) \quad (12)$$

As noted, Equations (9)-(12) may set forth the geometric constraints of the links ACK, CGHL, BDF, DG, FH, KM, and LMP. Equations (9)-(12) may be solved to optimize (e.g., minimize) the objective function set forth in Equation (13) below.

$$f = w_{pt} \sum_{j=0}^{N-1} \left( (\tilde{P}_j - P_j)(\overline{\tilde{P}_j - P_j}) \right) + w_{ang} \sum_{j \geq 1} \left( (\cos\tilde{\psi}_j - \cos\psi_j)^2 + (\sin\tilde{\psi}_j - \sin\psi_j)^2 \right) \quad (13)$$

wherein $w_{pt} = 0.1$ and $w_{ang} = 1$ may be weighting factors tuned during configuration of the link assembly 400, $P_j$ may be the position of the foot, $\tilde{P}_j$ may be the desired position of the foot, and $\psi_j$ may be the desired crank angle.

In some example embodiments, the pivot locations of the link assembly 400 may be determined by at least solving Equations (9)-(12) and minimizing the objective function set forth in Equation (13). Table 1 below sets forth the pivot locations for the link assembly 400.

TABLE 1

| | |
|---|---|
| A = −0.001830 + 0.021353i | B = 0.022500 + 0.036716i |
| C = 0.060743 + 0.047760i | D = 0.031343 + 0.034990i |
| F = 0.014782 + 0.036849i | G = 0.086637 + 0.061279i |
| H = 0.065686 + 0.061515i | K = 0.051913 + 0.045494i |
| L = −0.023710 − 0.030571i | M = −0.033708 − 0.030379i |
| $P_0$ = 0.022640 − 0.035994i | |

Figure 5:
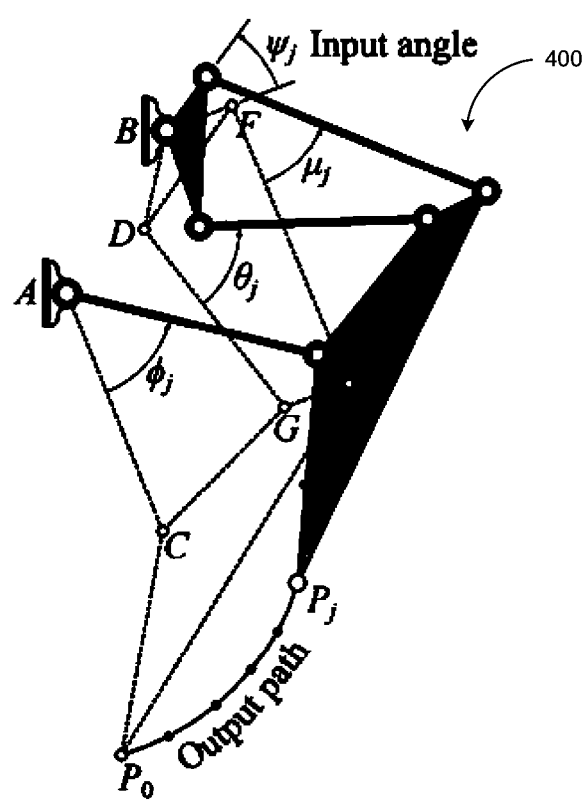
FIG. 5 depicts an alternative configuration for a link assembly, in accordance with some example embodiments.

FIG. 5 depicts an alternative configuration for the link assembly 400, in accordance with some example embodiments. Referring to FIGS. 4-5, the link assembly 400 may include six bars instead of the eight bars shown in FIG. 4. It should be appreciated that the link assembly 400 may include any number of bars forming any number of moving links. As noted, the quantity of links included in the link assembly 400, the respective lengths of the links, the respect mass of the links, and/or the pivot locations formed by the links may be configured such that the mechanical advantage of the resulting robotic limb varies (e.g., increases) as the link assembly 400 transitions from one configuration (e.g., a crouched configuration) to another configuration (e.g., an extended configuration).

Figure 6:
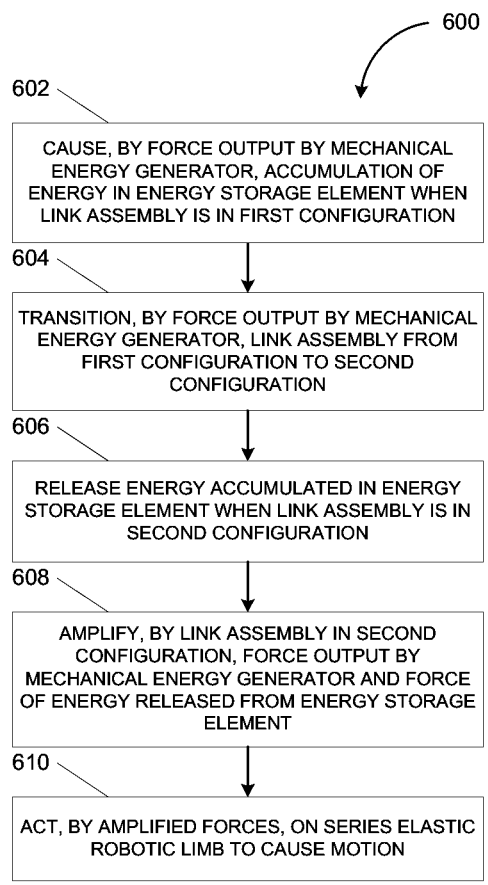
FIG. 6 depicts a flowchart illustrating a process for series elastic robotic locomotion, in accordance with some example embodiments.

FIG. 6 depicts a flowchart illustrating a process 600 for series elastic robotic locomotion, in accordance with some example embodiments. Referring to FIGS. 1-6, the process 600 may be performed by the series elastic robotic limb 150.

At 602, force output by the energy generator 170A may cause an accumulation of energy in the energy storage element 170B when the link assembly 170C is in a first configuration. For instance, in some example embodiments, the energy generator 170A may be the motor 210A while the energy storage element 170B may be the spring 210C. While the link assembly 170C is in a crouched configuration, force (e.g., torque) output by the motor 210A may deform the spring 210C and cause energy to accumulate in the spring 210C. As noted, when the link assembly 170C is in the crouched configuration, the mechanical advantage associated with the link assembly 170C may be low. Accordingly, while the force output by the motor 210A may cause the accumulation of energy in the spring 210C, that force may not be sufficiently amplified by the link assembly 170C to cause the series elastic robotic limb 150 to perform a motion such as, for example, a jump and/or the like. Referring to FIG. 3, this accumulation of energy in the energy storage element 170B may occur during an energy storage phase. It should be appreciated that the series elastic robotic limb 150 may be in this energy storage phase while the link assembly 170C is in the crouched configuration.

At 604, the force output by the energy generator 170A may transition the link assembly 170C from the first configuration to a second configuration, thereby increasing the mechanical advantage associated with the link assembly 170C. In some example embodiments, the force (e.g., torque) output by the motor 210A may further transition the link assembly 170C from the crouched configuration to an extended configuration. For instance, as noted, force output by the motor 210A may be transferred, via the first link 215A, to the rest of the link assembly 170C. This force may cause at least some of the links forming the link assembly 170C to pivot, articulate, and/or rotate about the joints coupling the links. For example, to transition the link assembly 170C from the crouched configuration to the extended configuration, the force output by the motor 210A may cause the third link 215C and the fifth link 215E to pivot at the third joint 220C, the fifth link 215E and the seventh link 215G to pivot at the sixth joint 220F, and/or the sixth link 215F and the seventh link 215G to pivot at the eighth joint 220H.

At 606, the energy accumulated in the energy storage element 170B may be released when the link assembly 170C is in the second configuration. As shown in FIG. 3, the series elastic robotic limb 150 may enter an energy release phase as the link assembly 170C transitions from the crouched configuration to the extended configuration. During the energy release phase, the energy that had built up in the spring 210C may be released.

At 608, the force output by the energy generator 170A and the force of the energy released from the energy storage element 170B may be amplified by the link assembly 170C in the second configuration. According to some example embodiments, the mechanical advantage of the link assembly 170C may reach a maximum when the link assembly 170C is in the extended configuration. Here, the link assembly 170C may amplify the force output by the motor 210A as well as the force from the energy released from the spring 210C. The amplification of these forces may provide sufficient power to trigger a motion such as, for example, a jump and/or the like.

At 610, the amplified forces may act on the series elastic robotic limb 150 and cause a motion. For example, amplified forces may be delivered to the foot 180 of the series elastic robotic limb 150 to cause the series elastic robotic limb 150 to perform a jumping motion. It should be appreciated that the power associated with this motion may exceed the power output of the motor 210A alone.

Figure 7:
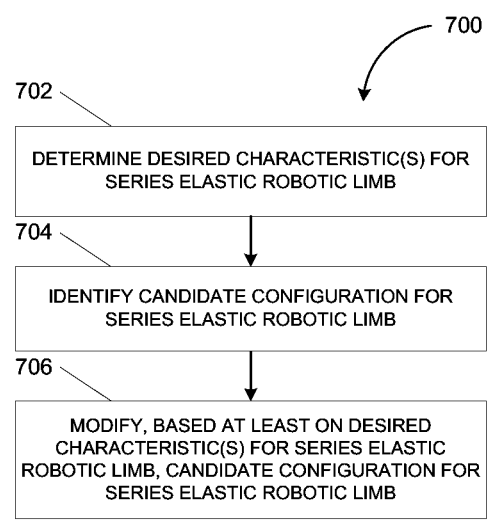
FIG. 7 depicts a flowchart illustrating a process for configuring a series elastic robotic limb, in accordance with some example embodiments.

FIG. 7 depicts a flowchart illustrating a process 700 for configuring a series elastic robotic limb, in accordance with some example embodiments. Referring to FIGS. 1-7, the process 700 may be performed in order to configure the series elastic robotic limb 150 including, for example, the link assembly 170C.

At 702, one or more desired characteristics may be determined for the series elastic robotic limb 150. In some example embodiments, the one or more desired characteristics may include, for example, application of a constant ground reaction force through a center of mass of the body 160, a variable mechanical advantage profile, a desired velocity of the output motion, a desired angular velocity, and/or the like.

At 704, a candidate configuration for the series elastic robotic limb 150 may be identified. For example, in some example embodiments, the candidate configuration may be identified based at least on the desired characteristics of the series elastic robotic limb 150 and may therefore exhibit at least some of the desired characteristics for the series elastic robotic limb 150. Alternatively and/or additionally, the candidate configuration may not exhibit any of the desired characteristics for the series elastic robotic limb 150.

At 706, the link assembly associated with the candidate configuration may be modified based at least on the desired characteristics. In some example embodiments, the link assembly may be modified by adjusting the quantity of links included in the link assembly, the respective lengths of the links, the respective mass of the links, the pivot locations, and/or the like. The link assembly may be modified such that the series elastic robotic limb 150 exhibits the desired characteristics including, for example, application of a constant ground reaction force through a center of mass of the body 160, a variable mechanical advantage profile, a desired velocity of the output motion, a desired angular velocity, and/or the like.

FIG. 8 depicts a block diagram illustrating a computing system 800, in accordance with some example embodiments. Referring to FIGS. 7-8, the process 700 may be performed on the computing system 800.

As shown in FIG. 8, the computing system 800 can include a processor 810, a memory 820, a storage device 830, and input/output devices 840. The processor 810, the memory 820, the storage device 830, and the input/output devices 840 can be interconnected via a system bus 850. The processor 810 is capable of processing instructions for execution within the computing system 800. Such executed instructions can implement one or more operations of the process 700. In some example embodiments, the processor 810 can be a single-threaded processor. Alternately, the processor 810 can be a multi-threaded processor. The processor 810 is capable of processing instructions stored in the memory 820 and/or on the storage device 830 to display graphical information for a user interface provided via the input/output device 840.

The memory 820 is a computer readable medium such as volatile or non-volatile that stores information within the computing system 800. The memory 820 can store data structures representing configuration object databases, for example. The storage device 830 is capable of providing persistent storage for the computing system 800. The storage device 830 can be a floppy disk device, a hard disk device, an optical disk device, or a tape device, or other suitable persistent storage means. The input/output device 840 provides input/output operations for the computing system 800. In some example embodiments, the input/output device 840 includes a keyboard and/or pointing device. In various implementations, the input/output device 840 includes a display unit for displaying graphical user interfaces.

According to some example embodiments, the input/output device 840 can provide input/output operations for a network device. For example, the input/output device 840 can include Ethernet ports or other networking ports to communicate with one or more wired and/or wireless networks (e.g., a local area network (LAN), a wide area network (WAN), the Internet).

In some example embodiments, the computing system 800 can be used to execute various interactive computer software applications that can be used for organization, analysis and/or storage of data in various formats. Alternatively, the computing system 800 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 840. The user interface can be generated and presented to a user by the computing system 800 (e.g., on a computer screen monitor, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus, comprising:
    an energy storage element;
    a link assembly comprising a plurality of links coupled, via one or more joints, at one or more pivot locations, the plurality of links having a relative length configured to achieve a variable mechanical advantage profile in which a mechanical advantage of the link assembly is at a minimum when the link assembly is in a crouched configuration, increases as the link assembly transitions from the crouched configuration to an extended configuration, and is at a maximum when the link assembly is in the extended configuration; and
    an energy generator configured to output a first force, the first force causing an accumulation of energy in the energy storage element when the link assembly is in the crouched configuration, and the first force further transitioning the link assembly from the crouched configuration to the extended configuration,
    wherein the energy storage element is configured to release the energy accumulated in the energy storage element when the link assembly is in the extended configuration, and
    wherein the link assembly in the extended configuration is configured to amplify both the first force output by the energy generator and a second force associated with the energy released from the energy storage element, the amplified first force and second force triggering a motion of the apparatus, wherein a force amplification achieved by the link assembly is variable based on respective lengths of the plurality of links, respective masses of the plurality of links, and the one or more pivot locations.

2. The apparatus of claim 1, wherein the plurality of links includes a first link and a second link coupled via a joint, and wherein the first link and the second link pivot about the joint in order to transition the link assembly from the crouched configuration to the extended configuration.

3. The apparatus of claim 2, wherein the first link and the second link pivot about the joint in response to the first force output by the energy generator.

4. The apparatus of claim 1, wherein the transition to the extended configuration maximizes the mechanical advantage associated with the link assembly, and wherein the force amplification is at a maximum when the mechanical advantage associated with the link assembly is maximized.

5. The apparatus of claim 1, wherein a displacement of the plurality of links from the crouched configuration to the extended configuration is quantified by respective angular displacement variables.

6. The apparatus of claim 5, wherein the apparatus further comprises a foot, wherein geometric constraints of the plurality of links are based on the respective angular displacement variables, wherein an objective function is based on the geometric constraints, a plurality of weighting factors, a position of the foot, a desired position of the foot, and a desired crank angle, and wherein the amplified first force and second force act on the foot to trigger the motion of the apparatus.

7. The apparatus of claim 6, wherein the one or more pivot locations are determined based on minimizing the objective function such that the foot exhibits a desired angular velocity.

8. The apparatus of claim 7, wherein the action of the amplified first force and second force on the foot triggers a ground reaction force when the foot makes contact with a surface, and wherein the ground reaction force causes the motion of the apparatus, and wherein the transition of the link assembly causes the foot to move in a straight path with respect to a body of the apparatus such that the ground reaction force traverses a center of mass of the apparatus and lacks rotational moments that cause a spinning motion of the apparatus.

9. The apparatus of claim 1, wherein the motion comprises a jumping motion.

10. A method, comprising:
    outputting, by an energy generator comprising an apparatus, a first force, the apparatus further comprising an energy storage element and a link assembly that includes a plurality of links coupled, via one or more joints, at one or more pivot locations, each link of the plurality of links having a relative length configured to achieve a variable mechanical advantage profile in which a mechanical advantage of the link assembly is at a minimum when the link assembly is in a crouched configuration, increases as the link assembly transitions from the crouched configuration to an extended configuration, and is at a maximum when the link assembly is in the extended configuration, the first force output by the energy generator causing an accumulation of energy in the energy storage element when the link assembly is in the crouched configuration, and the first force further transitioning the link assembly from the crouched configuration to the extended configuration;
    in response to the link assembly being transitioned to the extended configuration, releasing, by the energy storage element, the energy accumulated in the energy storage element; and
    amplifying, by the link assembly in the extended configuration, both the first force output by the energy generator and a second force associated with the energy released from the energy storage element, the amplified first force and second force triggering a motion of the apparatus, wherein a force amplification achieved by the link assembly is variable based on respective lengths of the plurality of links, respective masses of the plurality of links, and the one or more pivot locations.

11. The method of claim 10, wherein the plurality of links includes a first link and a second link coupled via a joint, and wherein the first force transitions the link assembly from the crouched configuration to the extended configuration by at least causing the first link and the second link to pivot about the joint.

12. The method of claim 10, wherein the transition to the extended configuration maximizes the mechanical advantage associated with the link assembly, and wherein the force amplification is at a maximum when the mechanical advantage associated with the link assembly is maximized.

13. The method of claim 10, wherein a displacement of the plurality of links from the crouched configuration to the extended configuration is quantified by respective angular displacement variables.

14. The method of claim 13, further comprising:
delivering, to a foot comprising the apparatus, the amplified first force and second force, the amplified first force and second force acting on the foot to trigger the motion of the apparatus, wherein geometric constraints of the plurality of links are based on the respective angular displacement variables, and wherein an objective function is based on the geometric constraints, a plurality of weighting factors, a position of the foot, a desired position of the foot, and a desired crank angle.

15. The method of claim 14, wherein the one or more pivot locations are determined based on minimizing the objective function such that the foot exhibits a desired angular velocity.

16. The method of claim 15, wherein the action of the amplified first force and second force on the foot triggers a ground reaction force, in response to the foot making contact with a surface, wherein the ground reaction force causes the motion of the apparatus, and wherein the transition of the link assembly causes the foot to move in a straight path with respect to a body of the apparatus such that the ground reaction force traverses a center of mass of the apparatus and lacks rotational moments that cause a spinning motion of the apparatus.

17. The method of claim 10, wherein the motion comprises a jumping motion.

18. An apparatus, comprising:
means for storing energy;
means for providing mechanical advantage, the means for providing mechanical advantage comprising a plurality of links having a relative length configured to achieve a variable mechanical advantage profile in which a mechanical advantage of the means for providing mechanical advantage is at a minimum when the means for providing mechanical advantage is in a crouched configuration, increases as the means for providing mechanical advantage transitions from the crouched configuration to an extended configuration, and is at a maximum when the means for providing mechanical advantage is in the extended configuration; and
means for generating energy,
wherein the means for generating energy outputs a first force, the first force causing an accumulation of energy in the means for storing energy when the means for providing mechanical advantage is in the crouched configuration, and the first force further transitioning the means for providing mechanical advantage from the crouched configuration to the extended configuration,
wherein the means for storing energy releases the energy accumulated in the means for storing energy when the means for providing mechanical advantage is in the extended configuration, and
wherein the means for providing mechanical advantage in the extended configuration amplifies the first force output by the means for generating energy and a second force associated with the energy released from the means for storing energy, the amplified first force and second force triggering a motion of the apparatus, wherein a force amplification achieved by the means for providing mechanical advantage is variable based on respective lengths of the plurality of links, respective masses of the plurality of links, and one or more pivot locations.

\* \* \* \* \*